US00PP21202P2

(12) United States Plant Patent
Khemakongkanond

(10) Patent No.: US PP21,202 P2
(45) Date of Patent: Aug. 17, 2010

(54) ***DISCHIDIA* PLANT NAMED 'SUPHA08'**

(50) Latin Name: *Dischidia hybrida*
Varietal Denomination: SUPHA08

(76) Inventor: Kanchana Khemakongkanond, 57 Phattanakan Lane 63 Off 2, Bangkok 10250 (TH)

( * ) Notice: Subject to any disclaimer, the term of this patent is extended or adjusted under 35 U.S.C. 154(b) by 27 days.

(21) Appl. No.: 12/221,434

(22) Filed: Aug. 2, 2008

(51) Int. Cl.
*A01H 5/00* (2006.01)

(52) U.S. Cl. ..... Plt./226

(58) Field of Classification Search ..... Plt./226, Plt./263.1
See application file for complete search history.

*Primary Examiner*—Kent L Bell

(57) ABSTRACT

A new and distinct *Dischidia hybrida* cultivar named 'SUPHA08' is disclosed, characterized by strong, durable green leaves, forming interesting, strongly convex shapes, appearing hollow. The new variety is a *Dischidia hybrida*, and naturally blooms continuously from Spring through Fall.

1 Drawing Sheet

Figure 1:
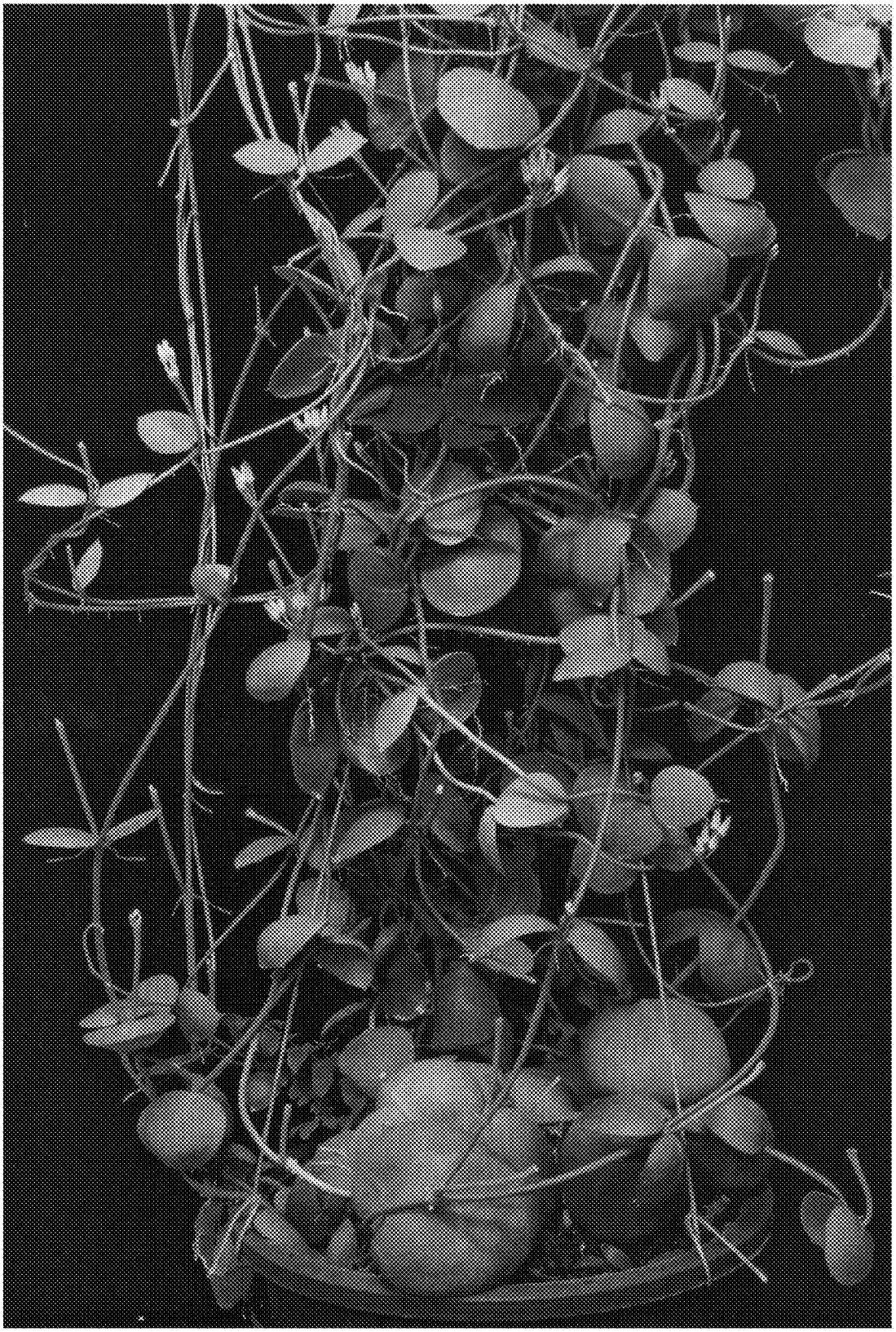

Latin name of the genus and species: *Dischidia hybrida.*
Variety denomination: 'SUPHA08'.

BACKGROUND OF THE INVENTION

The new cultivar is the product of a planned breeding program under the direction of the inventor, Kanchana Khemakongkanond, a citizen of Thailand. The objective of the breeding program was to produce plants of *Dischidia* suitable for commercial pot plant production. The new variety is the result of a crossing between the seed parent, an unnamed plant of the species *Dischidia pectinoides* and the pollen parent, an unnamed plant of the species, *Dischidia playphylla*. The new variety was discovered during 2007 by the inventor in a commercial greenhouse, in Chonburi, Thailand.

Asexual reproduction of the new cultivar 'SUPHA08' by vegetative cuttings was performed in Chonbury , Thailand and has shown that the unique features of this cultivar are stable and reproduced true to type through successive generations.

SUMMARY OF THE INVENTION

The cultivar 'SUPHA08' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHA08' These characteristics in combination distinguish 'SUPHA08' as a new and distinct *Dischidia* hybrid cultivar:

1. Highly convex leaves, forming interesting shape, appearing hollow.
2. Exceptionally broad leaves.
3. Unique green color of the foliage.

PARENT COMPARISON

Plants of the new cultivar 'SUPHA08' are similar to plants of the seed parent an unnamed plant of the species, *Dischidia pectinoides* in most horticultural characteristics. However, plants of the new cultivar 'SUPHA08' produce wider leaves than the seed parent.

Plants of the new cultivar 'SUPHA08' are also similar to plants of the pollen parent, an unnamed plant of the species, *Dischidia platyphylla*. However, plants of the pollen parent produce much flatter leaves than the new variety.

The parent plants are also the best commercial comparisons to the new cultivar.

BRIEF DESCRIPTION OF THE PHOTOGRAPH

The accompanying photograph in FIG. 1 illustrates in full color a typical plant of 'SUPHA08' grown in a greenhouse. The pot size is a commercial 10.5 cm container, approximately. The plant shown is approximately 9 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'SUPHA08' plants grown in a commercial greenhouse in Honselersdijk, The Netherlands from Fall to Spring. The growing temperature ranged from approximately 20 to 21° C. at night and 20 to 22° C. during the day. Measurements and numerical values represent averages of typical flowering types. No chemical or photoperiodic treatments were given.

Botanical classification: *Dischidia hybrida* cultivar 'SUPHA08.'

PROPAGATION

Time to rooting: About 10 to 20 days at approximately 25° C.

Root description: Small, fleshy, free-branching roots.

PLANT

Growth habit: Vining, upright tender perennial, suitable for indoor ornamental use.

Height: Approximately 52.4 cm.

Plant spread: Approximately 14.5 cm.

Growth rate: Rapid. Approximately 20 cm per month while actively growing.

Typical internode length: Approximately 8 cm.

Branching characteristics: Basally branching.

Length of stems: Average 56.3 cm.

Diameter of stems: Approximately 0.2 cm.

Quantity of stems: Average 3.

Texture of stems: Rounded, smooth, moderately glossy.

Color of stems: A color between RHS Green 137C and 138A.

Aspect: Upright, twining.

Number of leaves per stem: Average 12, in 6 pairs.

Other stem characteristics: Aerial roots form along stem, just below leaves, or in random locations on older stems.

*Average length of aerial roots.*—Approximately 3.2 cm.

*Average diameter of aerial roots.*—Approximately 0.1 cm.

*Color of aerial roots.*—Near RHS Yellow-Green 148D.

Age of plant described: Approximately 9 months old.

FOLIAGE

Leaf:

*Arrangement.*—Opposite, simple.

*Average length.*—Approximately 4.0 cm.

*Average width.*—Approximately 3.3 cm.

*Shape of blade.*—Broad ovate.

*Aspect.*—Young leaves slightly convexed. Older leaves strongly convexed.

*Apex.*—Short apiculate.

*Base.*—Cordate.

*Attachment.*—Stalked.

*Margin.*—Entire.

*Texture of top surface.*—Smooth, dull, leathery.

*Texture of bottom surface.*—Smooth, dull, leathery.

*Color.*—Young foliage upper side: Near R.H.S. Green 143B to Yellow-Green 144A. Young foliage under side: Near RHS Yellow-Green 144B. Mature foliage upper side: A color between RHS Green 137B and 137C. Mature foliage under side: Near RHS Green 138A.

*Venation.*—Type: Pinnate, insignificant, barely visible. Color same as leaf blade.

Petiole:

*Length.*—Average 0.1 cm.

*Width.*—Average 0.1 cm.

*Coloration.*—Near RHS Green 137C.

Other characteristics: Foliage produces a milky substance when damaged.

*Substance color.*—Near RHS Green-White 157D. No stipules, tendrils, thorns, or spines present.

FLOWER

Bloom period: Continuously sets buds, year-round in an indoor or greenhouse environment, at temperatures above 20° C. however. flowers do not open and drop in bud-stage.

Bud:

*Bud shape.*—Ovate.

*Bud length.*—Average 0.7 cm.

*Bud diameter.*—Approximately 0.2 cm.

*Bud color.*—Near RHS Yellow-Green 145C, Tip both Red-Purple 63C and 63D. Older buds, just before dropping change color to: Greyed-Yellow 161D, tip Red-Purple 58D.

Inflorescence:

*Form.*—Terminal and axillary, clusters.

*Width of entire inflorescence.*—Average 2.4 cm.

*Height of entire inflorescence.*—Average 1.4 cm.

*Quantity of individual flower buds in inflorescence.*—Avg. 17.

*Quantity of flower buds per lateral stem.*—Approximately 68.

*Duration on plant.*—Approximately 1 week. Self-cleaning.

Fragrance: None.

Peduncle:

*Length.*—Approximately 2.3 cm.

*Diameter.*—Approximately 0.2 cm.

*Angle.*—Average angle 70 degrees from stem.

Color.—Near RHS Green 138A.

*Strength.*—Strong.

Pedicels:

*Arrangement.*—Occurring singly.

*Length.*—Approximately 0.5 cm.

*Diameter.*—Approximately 0.1 cm.

*Angle.*—Central flower buds occur straight up, other flower buds at angles between 40 degrees and 80 degrees.

*Strength.*—Moderately strong.

*Color.*—Near RHS Yellow-Green 144A.

REPRODUCTIVE ORGANS

Not observed due to complete flower bud abortion.

OTHER CHARACTERISTICS

Disease resistance: Neither resistance nor susceptibility to diseases or pests has been observed in this variety.

Drought tolerance and temperature tolerance: Tender perennial, low temperature tolerance is unknown. Tolerates high temperature to at least 40° C. No drought tolerance has been observed.

Fruit/seed production: Fruits and seeds have not been observed.

What is claimed is:

1. A new and distinct cultivar of *Dischidia* plant named 'SUPHA08' as herein illustrated and described.

* * * * *